United States Patent [19]

Harte

[11] 4,133,639

[45] Jan. 9, 1979

[54] TEST ARTICLE INCLUDING A COVALENTLY ATTACHED DIAGNOSTIC REAGENT AND METHOD

[75] Inventor: Richard A. Harte, Redwood City, Calif.

[73] Assignee: International Diagnostic Technology, Inc., Santa Clara, Calif.

[21] Appl. No.: 663,828

[22] Filed: Mar. 4, 1976

Related U.S. Application Data

[63] Continuation-in-part of Ser. No. 553,582, Feb. 27, 1975, Pat. No. 3,992,631, which is a continuation-in-part of Ser. No. 447,574, Mar. 17, 1974, abandoned.

[51] Int. Cl.² .................... G01N 33/16; G01N 21/00
[52] U.S. Cl. ................... 23/230 B; 23/230.6; 195/103.5 R; 195/103.5 A; 250/365; 424/1; 424/7; 424/8; 424/12; 422/104
[58] Field of Search ............... 23/230 B, 253 R, 259, 23/230.6; 424/1, 1.5, 7, 12, 8; 195/103.5 R, 103.5 A

[56] References Cited

U.S. PATENT DOCUMENTS

| | | | |
|---|---|---|---|
| 3,646,346 | 2/1972 | Catt | 424/12 X |
| 3,720,760 | 3/1973 | Bennich | 424/1 |
| 3,826,619 | 7/1974 | Bratu | 23/253 R |
| 3,935,074 | 1/1976 | Rubenstein | 424/12 X |
| 3,973,129 | 8/1976 | Blumberg | 23/230 B |

OTHER PUBLICATIONS

R. Axen et al., Nature, vol. 214, 1302-1304 (Jun. 24, 1967).

"Radioimmunoassay Methods", European Workshop, Sep. 15-17, 1970, Edinburgh, Kirkham et al., eds.
Envall et al., Biochim. Biophys. Acta., 251 (1971) 427-434.
"Solid Phase Radioimmunoassay of Human Growth Hormone", Catt et al., J. Lab. & Clin. Med., (1966) 100, 31c.

*Primary Examiner*—Sidney Marantz
*Attorney, Agent, or Firm*—Flehr, Hohbach, Test, Albritton & Herbert

[57] ABSTRACT

A body suitable for use in the quantitative detection of an unknown quantity of a biologically derived sample suitably by radioimmunoassay, fluorometric detection, or by spectrophotometry. The body includes a handle attached to a nonparticulate, nonswellable, impermeable continuous surface region. A diagnostic reagent (e.g., an antibody) is covalently attached to the surface region. The surface region is stirred by the handle in a solution of sample substance (e.g., antigen) for reaction with the diagnostic reagent. In a competitive binding technique, a labelled substance (e.g., fluorochrome labelled antigen) is simultaneously contacted with the sample. Thereafter, the surface region is washed, and the label is measured as by a fluorometer. The technique is also applicable to the so-called "sandwich technique" in which the labelled substance (e.g., labelled antibody) is reacted with the sample substance after it has been reacted with the diagnostic reagent. The above type of surface facilitates simple and effective separation of bound from free labelled substance and allows thorough washing to cleanse the surface of residual free and nonspecifically bound labelled substance.

13 Claims, 3 Drawing Figures

U.S. Patent  Jan. 9, 1979  4,133,639
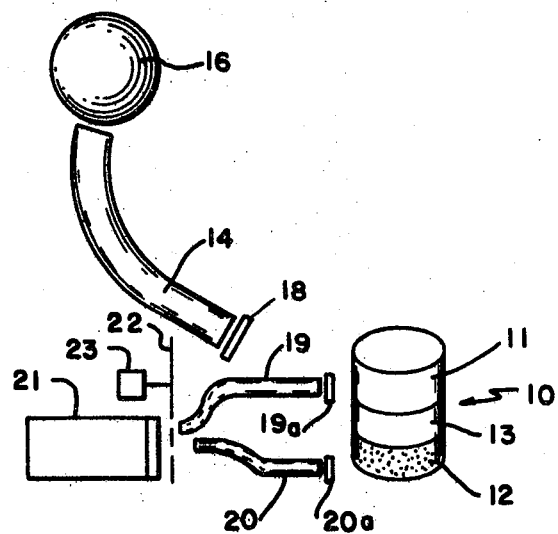
FIG.—1
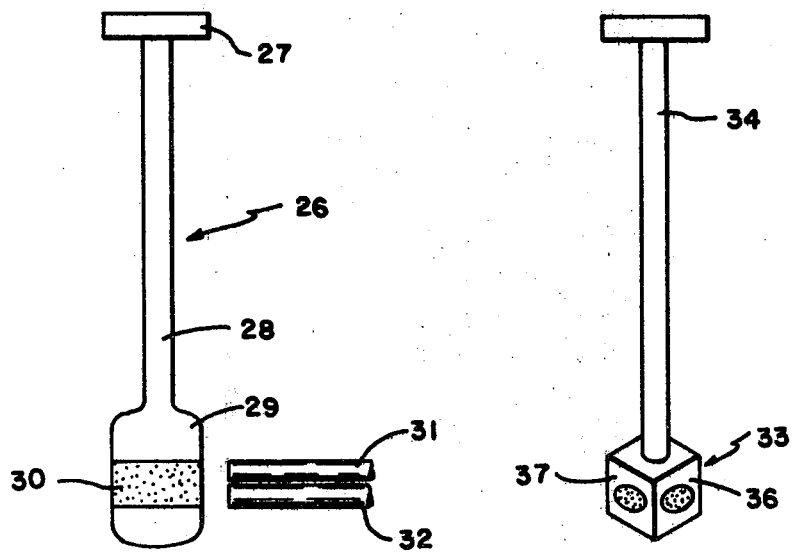
FIG.—2  FIG.—3

TEST ARTICLE INCLUDING A COVALENTLY ATTACHED DIAGNOSTIC REAGENT AND METHOD

CROSS-REFERENCE TO RELATED APPLICATION

This application is a continuation-in-part of application Ser. No. 553,582, filed Feb. 27, 1975, now issued as U.S. Pat. No. 3,992,631, dated Nov. 16, 1976, which is a continuation-in-part of application Ser. No. 447,574, filed Mar. 17, 1974, abandoned.

BACKGROUND OF THE INVENTION

There are a multitude of techniques employed for the quantitative determination of an unknown quantity of a sample derived from a biological fluid (e.g., serum or urine). Techniques based upon radioactive labelled substance include indirect (competitive binding, saturation or displacement) and direct (sandwich and immunoradiometric) radioimmunassays. Other known techniques are based on fluorochrome and enzyme labels. After completion of the above reactions, the labelled substances which have been bound must be separated from the unreacted labelled substance which includes free and non-specifically bound substance. This separation step in liquid form can be inefficient, unreliable and inconvenient.

A number of techniques have been proposed to solve this problem by use of diagnostic reagents on solid surfaces which combine with the labelled substance. In each of these systems, the solid substrate containing the bound labelled substance is separated from the liquid phase containing the free labelled substance and is thereafter washed to remove the residual free and the non-specifically bound labelled substance.

In one technique for the detection of antigen, reagents are coated upon plastic test tubes or inserts by the physical adsorption of antibodies specific to the sample substances to be tested. Such techniques are disclosed in U.S. Pat. Nos. 3,646,346 and 3,826,619. Such physical adsorption is difficult to control because of the non-uniformity of plastic surfaces as well as imprecision in the coating techniues. See, e.g., the work entitled "Radioimmunoassay Methods", European Workshop, Sept. 15-17, 1970, Edinburgh (Editors Kirkham et al). At page 441, the authors state that the amount of binding is between 20% and 70% using various coated polystyrene tubes in a particular system, which led to the abandonment of this technique. Furthermore, in subsequent immunochemical reactions, a significant amount of "non-specific" binding of the labelled substance to the solid surface occurs. This binding, of a hydrophobic or ionic nature, is weaker than the immunochemical bond. Hence, vigorous and repeated washings required to effectively remove solution residual and non-specifically bound labelled substance frequently disrupts the weaker physical coated bond resulting in the loss of physically bound diagnostic reagent. The results of assays employing such coated surfaces are thus relatively imprecise and non-reproducible because of these kinds of misclassification errors. (Envall et al., *Biochim. Biophys. Acta*, 251 (1971) 427–434, at p. 430). Another disadvantage of physically coating as with antibodies is that the antibodies in that form are relatively unreactive with large antigens. It is believed that this is due to steric hindrance effects.

In the technique of Bennich et al U.S. Pat. No. 3,720,760, immunological substances are more firmly secured by attachment to porous microreticular swellable polymer of the type sold under the trademark "Sephadex". Such material is indicated as being preferably in particulate form. Such microreticular materials have the inherent disadvantage of being difficult to wash their interstitial void spaces free of non-specifically bound and entrained free labelled substance. This results in undesirably high background readings. Also, it is difficult to rinse the interparticulate void spaces sufficiently free of residual free labelled substances, generally requiring several displacement washes. Each washing step requires a centrifugal and careful decantation separation to avoid misclassification to minimize inadvertent spillage of particles during the washing procedure.

This technique is unsuitable in fluorometric and colorimetric surface systems because the particles cannot be accurately viewed. This is because loose microreticular beads used in radioactive assays produce an ill-defined and difficult to control surface for uniform illumination and viewing.

Another technique which has been proposed is described in an article entitled "Solid Phase Radioimmunoassay of Human Growth Hormone" by Catt et al, *J. Lab. & Clin. Med.*, (1966) 100, 31c. Small discs of substituted graft copolymer sold under the trademark "Protapol DI/1", are coated with antibody. As set forth in the above Kirkham et al work, at pages 294 and 295, this technique yields poor replication, i.e., there is a very wide scatter between the replicates at any given point, and sometimes the differences are very large. The discs require repeated handling and each time they are touched by a solid object the chance for loss of bound labelled substance or contamination by free labelled substance or other background contributing contaminants is considerable. Like the above particle technique, the disc would not be accurately viewed in fluorometric or colorimetric systems and would be difficult to manipulate into proper viewing relationship with an optical instrument.

In view of the foregoing, there is an apparent need for a solid phase analytical technique in which the surface is easy to wash, separations are easy to make, which is efficient and reproducible, and which can be presented easily for accurate viewing.

SUMMARY OF THE INVENTION AND OBJECTS

In accordance with the present invention, a body is provided which is suitable for use in the labelled quantitative determination of a biologically derived sample. The body includes a handle attached to at least one non-particulate, nonswellable, impermeable continuous surface region covalently attached to a diagnostic reagent which is reactive with the biologically derived sample. The surface with the attached reagent (e.g., antibody) is reacted with the sample substance (e.g., antigen). In one competitive technique, the labelled substance (e.g., fluorochrome-labelled antigen) is simultaneously reacted with the sample substance. In a sandwich technique, the labelled substance (e.g., fluorochrome-labelled antibody) is subsequently reacted. In another type of competitive technique, the attached reagent and sample substance are the same, and they both are simultaneously reacted with labelled substance, (e.g., fluorochrome labelled antibody). In any of these techniques, the reaction of the surface and sample is accelerated by stirring with the handle. Then, the surface is conveniently separated from the sample and transported by the handle of the body to a detection station for measuring the amount of labelled substance without need to touch the surface.

In one embodiment, the body includes at least two attached diagnostic reagent regions in which one contains a standard region of a predetermined quantity of the labelled substance. In another embodiment, the body is polyhedral and has a different diagnostic reagent on each of a plurality of its faces. Also, a plurality of diagnostic reagents may be attached in a single region in random dispersion and reacted with at least two different sample substances and labelled substances which emit different signals.

It is an object of the invention to provide a body and method for use in the labelled quantitative detection of a biologically derived sample which overcomes the aforementioned washing, separation, and handling problems of solid phase techniques of the prior art.

It is another object of the invention to provide a body of the foregoing type with a handle which facilitates non-touchable handling of the solid surfaces and eliminates the need to centrifuge and decant.

It is a particular object of the invention to provide a body and method of the foregoing type which can be employed for reproducible precise sample detection with low background noise and minimal misclassification error.

It is a particular object of the invention to provide a device and method of the foregoing type which is particularly adapted to precise and reproducible viewing in an optical system such as a fluorometer or colorimeter.

Further objects and features of the invention will be apparent from the following description of its preferred embodiments taken in conjunction with the accompanying drawings.

BRIEF DESCRIPTION OF THE DRAWINGS

FIG. 1 is a schematic view of one embodiment of the body of the invention viewed by a fluorometric system.

FIGS. 2 and 3 are different embodiments of the body of the system.

DETAILED DESCRIPTION OF THE PREFERRED EMBODIMENTS

The present invention relates to a body suitable for use in the labelled quantitative determination of a biologically derived sample substance. As is defined herein, the term "sample substance" is one which is contained in a biological fluid. Sample substances include antigens, antibodies, hormones, enzymes, drugs, infectious agents and other substances. The sample substance is reacted with a diagnostic reagent covalently attached to a continuous solid surface. As defined herein, "diagnostic reagent" is one which is attached to a surface and specifically reacts directly or indirectly with the sample substance. The diagnostic reagent is further reacted with a labelled substance for quantitative measurement. The term "labelled substance" is defined as a substance which includes a material detectible by a detection device and which is specifically reactive with the sample substance or diagnostic reagent. The sample substance itself sometimes may be autofluorogenic (e.g., tetracycline or enzymatic, e.g., trypsin) or can be made so in situ. Labels include fluorochromes, radionuclides and enzymes.

The labelled substances may be reacted with the sample substance before or after isolation, or may be linked to the solid surface with homologous labelled materials (e.g., antigen or antibody, one of which has been labelled).

For simplicity of description, the present specification will first describe a typical fluorometrically labelled system of the sandwich type. The procedure may be summarized as including the following steps:

(1) diagnostic reagent (e.g., antibody) is covalently attached to a surface region of a solid body;

(2) the attached diagnostic reagent is reacted with a sample substance (e.g., antigen) and bound to the surface region;

(3) the surface region is washed to remove unbound sample and solvent;

(4) the surface region is reacted with labelled substance (e.g., fluorochrome-labelled antibody);

(5) the surface region is again washed; and (6) the body is transported to a detection station to measure the amount of labelled substance.

Referring to step one, the diagnostic reagent, antibody, is covalently attached to a nonparticulate, nonswellable, impermeable, continuous surface region of the body. Such covalent attachment may be performed directly between the diagnostic reagent and a surface reactive with the same. Examples of such surfaces include polymers such as polymethylmethacrylate, polystyrene, polyamide (nylon) and polysaccharides. Diagnostic reagents having carboxylic acid and amino groups are reactive with such surfaces.

In an indirect coupling technique, groups reactive with the above groups serving as bridges between the polymer surfaces and the diagnostic reagent may either be present in the basic polymer or coupled thereto by known chemical reactions. Such coupling reagents include amino groups, hydroxyl groups, mercapto groups, amido groups, and carboxyl groups. Suitable coupling techniques between the polymer and diagnostic reagent are set forth in Bennich et al. U.S. Pat. No. 3,720,760.

Other covalent linkages may be performed indirectly with ceramic substrates by use of intermediate coupling agents as set forth in Weetall U.S. Pat. No. 3,652,761. Although that patent describes the coupling to microreticular surfaces, the techniques are also applicable to the continuous impermeable nonparticulate surface of the present body.

The so-called direct sandwich technique is performed as follows. A coupling reagent is first attached to the substrate. In one specific coupling technique, a polymeric surface, e.g., an acrylic, may be reacted with a coupling agent or spacer arm in a carbodiimide catalyzed nucleophilic substitution type reaction. Thereafter, the diagnostic reagent, e.g., antibody, is similarly covalently attached to the coupling agent.

In the following step, the body surface with covalently attached antibody is contacted with a fluid suspected of containing sample substance, e.g., antigen, reactive with the antibody. If present, the antigen reacts with and combines to the antibody on the surface during an incubation period. It is highly advantageous to agitate the reactive surface during incubation. This provides a significantly faster reaction time. In addition, it has been found to increase the reproducibility of the experimental results. For this purpose, as set forth hereinafter, the body is provided with a handle which can be used to stir the reactive surface region either mechanically or manually.

In the next step, after incubation with the sample serum containing antigen, the surface is simply separated from the solution and the surface is washed with a suitable solvent such as aqueous phosphate buffer or distilled water.

In the following step, the surface is contacted with a labelled substance, antibody solution labelled with a fluorochrome. The solution is again incubated for a sufficient time to complete the reaction between the labelled antibody and antigen. As with the incubation of sample, it is advantageous to agitate the solution during this incubation to decrease the reaction time as well as improve the reproducibility of the detection.

In the next step, the solution containing unbound labelled antibody is separated from the solid surface containing bound labelled antibody.

Subsequently, the reacted solid surface is thoroughly washed to remove residual free and nonspecifically bound antibody which may remain on the solid surface. The efficiency of this washing step is extremely important in obtaining accurate results. Thus, the surface is thoroughly washed with a suitable rinsing solution such as aqueous phosphate buffer or distilled water.

This washing step establishes the importance of the initial covalent attachment of the diagnostic reagent with the solid surface in the first step. If, for example, such reagent were merely coated as by adsorption on the solid surface, a portion of it together with accompanying labelled substance can be washed away during this vigorous washing procedure.

After washing, the body containing the labelled substance is transported to a detection station to measure the amount of the same. A particularly advantageous system for a fluorochrome-containing substance and the detection system is a fluorometric system of the type set forth in my application Ser. No. 447,574, filed Mar. 17, 1974. That system is incorporated herein by reference.

By way of background, one standard technique for binding sample substances to substrate is called by immunologists the "Sandwich Technique". In the conventional case, an antibody to the specific disease whose presence is being determined, is coated to the surface. A typical case uses the test for "Australian Antigen" in the blood which is regarded as prima facie evidence of hepatitis infection. The antiAustralian antigen-antibody is coated in a film to the plastic substrate. The serum of the subject suspected of carrying the antigen is reacted with the antibody. If the antigen is present, it binds immunologically to the antibody. After a rinse with water to remove all unbound material, more antibody with a fluorescent label is added. It binds to the antigen if it is present. Then a final rinse removes all unbound labelled antibody. Such a technique is described in Bratu U.S. Pat. No. 3,826,618 with respect to RIA. In the present invention, the antibody is first covalently attached to the surface. In a fluorometric system, the fluorescence, if any, emitted from the surface is detected by a fluorometer.

In another type of direct technique, the diagnostic reagent, e.g., antibody, is first covalently attached to the substrate as set forth above. Thereafter, the sample containing antigen, previously labelled as with fluorogen is contacted with the surface for immunological reaction between the antigen and antibody. The surface is then read by a fluorometer. This system is illustrated in Example 1, supra.

In another example of a sandwich technique, the body is covalently attached with antigen — a preparation of Treponema pallidum, for instance, if it is desired to determine antibodies for syphilis in the subject. The serum of the subject is incubated with the body, then rinsed. Then labelled antihuman antibodies (harvested from goat or rabbit) are added, incubated and rinsed. If human antibody for treponemae was present in the serum, then it adhered to the body by immunoreaction and, in turn, captured the labelled antibodies from the goat, for example, hence, a quantitative reading of titre for syphilis can be obtained. This is a modification of the standard accepted FTA-ABS Test (fluorescent treponemal antibody-adsorption) whereby the body system of this invention enables accurate quantitation.

Any infectious disease producing antibodies would be amenable to assay by this technique and includes such diseases of public health interest as: syphilis, gonorrhea, "strep" throat infection, dysentry, salmonella infection, typhoid, rabies, serum hepatitis, influenza types, etc. This invention can also be useful in quality control in the food and pharmaceutical industries.

Also, as another application emplyong the predescribed techniques, it is often of value not only to diagnose the presence of disease (antigens) but determine the body's protective immunity to disease (antibody titre) as a result of deliberate innoculation or vaccination. As an example, a physician innoculates a child with D.P.T. vaccine to provide immunity to diptheria, pertussis or whooping cough, and tetanus. He then assumes that all 3 have "taken". A test of the serum for antibody for each would, in fact, determine if all 3 antigens were effective in creating sufficient immunizing antibodies. Present technology does not allow this simple screening procedure.

When the method of the present invention is used in the so-called competitive technique, the foregoing systems are modified generally as follows. Instead of coupling diagnostic reagent (antibody)-sample (antigen)-labelled substance (antibody), the labelled substance and sample of the same type (e.g., antigen) are added simultaneously to compete with each other for diagnostic reagent (e.g., antibody) covalently attached to the solid surface. After this incubation or contact time, the solid surface is washed with the same advantages as the sandwich technique.

Illustrations of the system of this invention where antigens or antibodies in the strict sense are not involved but where protein-binding procedures are still employed include such combinations as thyroxine-binding globulin (TBG) and thyroxine ($T_4$), intrinsic factor and vitamin $B_{12}$, and bovine lactoglobulin and folic acid, for example.

In all cases, one of the pair (a first type of protein) may be covalently attached to a solid surface and may also bind with and remove from blood serum the other member of the pair (a second type of substance capable of binding to the protein of the first type), competing with fluorochrome-labelled molecules of its own type. These examples and the generalized use are strictly analogous to the antibody-serum antigen-labelled antigen systems described in several of the immunological reactions.

In the present specification, diagnostic reagent comprises one of the above pair and the biologically derived substance includes the other two. The reaction product of the pair of substances are "bound" to each other.

In another type of competitive technique, a known quantity of antigen is covalently attached to the surface and is contacted with specific labelled antibody simultaneously with a solution of the same type of antigen of unknown quantity. An RIA technique employing the above technique with a noncovalently bound surface in which radioactively labelled antibody in solution is measured is described in a paper by J. S. Woodhead, et al., entitled "The Immunoradiometric Assay and Related Techniques", *Br. Med. Bull.* 30:44 (1974). In the present system, the antigen is covalently attached to the surface, the labelled antibody on the surface is measured, and a fluorescent label is preferred.

Variations can include the use of a variety of fluorescent labels such as lissamine-rhodamine B, D.A.N.S. (1-dimethylamino-napthalene-5-sulfonic acid) orthophthaladehyde, and fluorescamine, which are frequently used in fluorescence microscopy. The first two possess an orange or red emission spectra rather than the yellow green or fluorescein and the second two possess a blue or green emission spectra. The only variation in the fluorometer would be the change in excitation and emission filters used, as well as the change in the fluorescent label on the antibodies in the reagent kit.

The present technique is also applicable to the use of enzyme labelled systems. One such system is described in an article by Pesce et al. entitled "Use of Enzyme-Linked Antibodies to Measure Serum Anti-DNA Antibody in Systemic Lupus Erthyematosus", *Clin. Chem.* 20/3, 353–359 (1974). The described system differs from the one described herein in that the diagnostic reagent, DNA, is adsorbed to a test tube support. Thereafter, serum containing DNA antibodies is reacted with the coated tube followed by reaction with an anti-human gamma globulin peroxidase enzyme conjugate with the coated tube. Then a colored reaction product is developed by action of peroxidase on the substrate which is colorimetrically measured by conventional techniques.

The following description will make particular reference to the body employed for use in the above techniques. It includes two important characteristics; a handle means and at least one nonparticulate, nonswellable, impermeable, continuous surface region capable of covalent attachment to a diagnostic reagent. The handle means may be the side of a test tube or a portion of a solid object. A particularly preferred handle means is a handle specifically formed to facilitate mechanical or manual handling of the body as for stirring or the like.

Referring specifically to FIG. 1, a body is illustrated in conjunction with a fluorometric system. The body 10, has been bound with a standard fluorescent labelled substance, 11, i.e., of the same fluorescent substance as is used to label the antibody containing surface 12 at the lower portion of cylinder 10 and has a known titre as measured on the detection device which is employed in the test tube or assay; in this instance, a fluorometer. Suitably a blank space 13 is left around the surface of the cylinder 10, separating the upper and lower layers 11 and 12, respectively. The lower layer 12 may contain streptoccocal fluorescent-labelled antibody prepared in any of the foregoing methods. The lower layer is immersed in the body liquid to determine if any of the suspected antigen or antibody is present in the serum being tested.

A fiber optical cable 14 conducts ultra-violet light from a light source 16. The light then passes through a suitable gelatin filter 18 which ensures that only light of the excited wavelength reaches the body and strikes the body surface whereupon it excites fluorescence of the fluorochrome labelled substance. Two fiber optical cables 19 and 20 are provided with respective filters 19a and 20a. One such cable 19 conducts fluorescent light from the standard fluorescent coating to a photomultiplier tube 21, and the other such cable 20 conducts emitted fluorescence from the lower fluorescent layer 12 to the photomultiplier tube 21. A chopper wheel 22 operated by motor 23 revolves and alternates the flow of light from each coating 11 and 12 to tube 21. In this manner, a direct comparison is obtained between the standard and test portions.

In the embodiment of FIG. 2, a paddle shaped body 26 includes a handle 27, a stem 28, and a wide, flat head 29 at the other end, the head 29 bearing a layer 30 of sample. In this embodiment, a fluorometer is illustrated in which two fiber optic cables 31 (for excitation light) and 32 (for emitted fluorescent light) are parallel to each other.

In the embodiment of FIG. 3, a multiple test body is illustrated. The body includes a cube 33 at the end of handle 34. The cube 33 can present four faces, two faces 36 and 37 being visible. Each face has a different sample layer. This body is particularly adapted for fluorometry. Thus, four different fluorescent labels can be provided, and the fluorometer may have a filter wheel with four selected wavelength regions to isolate energy going to photomultiplier tube 21. As the operator rotates the tube 33 (or other multifaceted polyhedron body), each test can be read in sequence. A handle can similarly be attached to a cylinder, sphere or other substrate. Other means of moving the substrate upon which different biologically-derived substances are layered may be employed to vary the surface exposed to the fluorometer.

Broadly stated, the banded cylinder of FIG. 1 and the cube of FIG. 3 constitue two forms of the use of multiple areas coated on the substrate adapted for rapid multiple quantitative determination, especially of the fluorometric type. Any shape of substrate may be employed so long as it includes a first area of sample substrate labelled as with a fluorochrome and at least one other area of such labelled substance. Such different areas may include a standard area of predetermined quantity of the same type of substance as the fluorochrome-labelled substance. In this manner, two different areas, such as bands 11 and 12 of FIG. 1, may be viewed to provide a direct comparison of the standard and test portions. Techniques for accomplishing this determination are set forth in my application, entitled "Fluorometric System, Method and Test Article", filed Feb. 27, 1975, Ser. No. 553,582.

In another embodiment, a single surface region may include a plurality of labelled substances in random dispersion chemically attached to the substrate. At least two of the labels for the sample are fluorochromes which emit fluorescense responsive to different wavelengths of light. These may be employed in cases where it is desirable to detect the presence of more than one sample substance.

To detect the above randomly dispersed labelled substances of different wavelengths, a fluorometer may be equipped with a filter wheel so that several different wavelengths can be selected for several particular fluorescent labels, e.g., (1) fluorescein isothiocyanate, (yellow-green); (2) lissamine rhodamine B-200 (deep orange); (3) D.A.N.S. (1-dimethylamino-napthalene-5-sulfonic acid; red); (4) ortho-phthaladehyde (blue-green); and (5) fluorescamine (blue-green) and when each label is attached to a different antibody for three microorganisms of interest in urinary tract infections (*E. coli*, Pseudomonas, and Staphylococcus), then one, two or all three may be simultaneously determined and identified.

Fluorescent label substances include sodium fluorescein isothiocyanate or other suitable substances. This particular fluorochrome having an excitation at 460 nanometers and emission at 520 nanometers is advantageous.

The surface region of the body is characterized by certain physical and chemical properties. The primary chemical property, set forth above, is its ability to covalently attach with the particular diagnostic reagent. With respect to the physical properties, such surface is nonparticulate, nonswellable, impermeable and continuous.

The nonparticulate nature of the body surface region distinguishes it from microbeads or the like. It should have a sufficient surface area to present a microscopic single surface to the detector to enable integration of the fluorescent light or radioactivity from large aggregates of labelled substances thereby reducing sampling errors from sample to sample. Suitably such area is at least 1 millimeter square. The use of such loose particles, often used in radioactive assays, produce an ill-defined and difficult to control surface for uniform excitation and precise viewing of fluorescence.

Another characteristic of the surface is that it is impermeable to liquid. This distinguishes from gel-like microrecticular beads. When such beads are employed for this purpose as set forth in the background, it is extremely difficult to wash their interstitial spaces free of nonspecifically bound and entrapped label reagent. by the use of impermeable surfaces, the washing procedure is faster and more efficient.

Another characteristic of the surface region is that it be continuous. This feature is related to impermeability. By formation of a continuous non-porous surface, the aforementioned difficulties of washing are avoided. It should be understood that a surface treated with acid or other reagent to assist coupling is within the scope of the invention even though the surface may be roughened. Any porosity, permeability, or discontinuity of such a roughened surface is negligible in comparison to the microreticular particles of the prior art.

Another feature of the surface region is that it be nonswellable. This contrasts to the three-dimensional gels such as Sephadex which are difficult to wash free of unbound reagents and to control dimensionally.

EXAMPLE 1

This example illustrates a fluorescent measurement of an antibody-antigen rection in which an antigen in solution is fluorescently labelled and reacted with an antibody immobilized on a surface. In this so-called "direct" technique, the fluorescence of the surface is proportional to the antigen concentration in solution.

Acid soaked polyamide strips were coated with Anti-Streptolysin O by immersing them for 30 minutes in a slowly stirred solution of Anti-Streptolysin O diluted 1:8 in saline solution while 1% of a coupling agent, glutaraldehyde was slowly added. After water washing and drying the covalently attached strips were exposed to various concentrations of Streptolysin O Toxin in distilled water. Two ml of each concentration were first reacted with 0.2 ml of fluorescamine solution (40 mg in 100 ml acetone) to affect labelling of the antigen. The strips were then added and stirred for 30 minutes, removed, water rinsed, and allowed to dry. They were then placed in the instrument, excited at a wavelength of 375 nm and fluorescence measured at a wavelength of 475 nm. The following results were obtained.

| Streptolysin O Toxin Dilution | Fluorescent Signal |
| --- | --- |
| 1:5 | 280 |
| 1:10 | 155 |
| 1:20 | 105 |
| 1:40 | 45 |
| 1:1000 | 5 |
| Blank | 0 |

EXAMPLE 2

This example illustrates a fluorescent measurement of bacteria in which bacteria in suspension are bound to a surface and reacted with fluorescently labelled antibody, in a so-called "sandwich" technique. The fluorescence of the surface is proportional to the bacterial concentration of the sample.

A pure culture of Streptococcus beta-hemolyticus Type A was grown in trypsin broth, autoclaved, centrifuged, and washed with phosphate buffer saline (PBS). The cells were resuspended in PBS to concentrations of $10^7$, $10^5$, and $10^3$ organisms per ml.

DEAE-cellulose strips were coated with Strepococcus A Antiserum by immersing them for 15 minutes in a stirred solution of antiserum diluted 1:16 in phosphate buffer while 0.5 ml of 50% of coupling agent, glutaraldehyde, was slowly added. After washing, the covalently attached individual strips were incubated for 5 minutes in 5 ml of each of the concentrations mentioned above, followed by washing with PBS.

Next, the strips were incubated for 5 minutes in a solution of fluorescein isothiocyanate labelled Streptococcus A antibody diluted 1:4 in phosphate buffer, rinsed with buffer and air dried. The strips were then placed in the instrument and the following readings were obtained.

| Streptococcal Concentration Organisms per ml. | Fluorescent Signal |
| --- | --- |
| $10^7$ | 840 |
| $10^5$ | 305 |
| $10^3$ | 122 |

While in this example, attachment was obtained by the cross-linking of antiserum proteins into a strongly adhering film, covalent attachment directly to cellulose derivatives such as amino-cellulose are similarly possible.

EXAMPLE 3

This example describes the fluorescent measurment of multiple surfaces that have been exposed to a common solution containing several substances for which measurement is desired.

Three squares of cellulose were each reacted with a different immunoglobulin antibody (goat anti-human IgA, IgG, and IgM) using glutaraldehyde coupling agent. The cellulose squares mounted on a plastic strip are placed in a sample of serum diluted in suitable buffer. After incubation for ten minutes, the strip is removed and the three coated squares rinsed with buffer. They are then reacted with a solution containing equally active concentrations of fluorescein isothiocyanate labelled goat anti-human IgA, IgG, and IgM diluted in suitable buffer and allowed to incubate another ten minutes. The strips are again washed and each area is separately read in the instrument. The relative concentrations of the various immunoglobulins are so determined.

EXAMPLE 4

This example describes the fluorescent measurement of a common surface exposed to a solution containing several substances for which individual measurements are desired.

A circular disc of polymethylmethacrylic acid containing a random mixture of the same three different immunoglobulin antibodies as set forth above are exposed to a sample of serum diluted in suitable buffer. After incubation for ten minutes, the strip is removed and rinsed with buffer. It is then incubated in a solution containing a mixture of goat antibodies to these immunoglobulins, each antibody labelled with a different fluorochrome, i.e., fluorescamine labelled goat anti-IgA, fluorescein isothiocyanate labelled goat anti-IgG, and rhodamine labelled goat anti-IgM diluted in suitable buffer and incubated for twenty minutes. The strip is removed and washed with buffer. It is then read sequentially in the instrument exciting first at 390 nm and reading emission at 485 nm, then at 480 nm and 520 nm, respectively, and finally at 520 nm and 595 nm, respectively. The concentrations of IgA, IgG, and IgM are so determined.

it will be understood that the above specific description and drawings have been given for the purposes of illustration only and that variations and modifications can be made therein without departing from the spirit and scope of the appended claims.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

What is claimed is:

1. A body suitable for use in the fluorometric detection of a biologically derived sample, said body comprising handle means connected to at least one nonparticulate, nonswellable, impermeable, continuous, flat surface region defining an area of at least one square millimeter and a diagnostic reagent bound to at least one biologically derived sample labelled with a fluorochrome, said diagnostic reagent being covalently attached to said surface region.

2. The body of claim 1 in which said surface region includes a plurality of said labelled sample substances attached to said diagnostic reagent in random dispersion, at least two of the fluorochrome labels for said sample emitting fluorescence responsive to different wavelengths of light.

3. The body of claim 1 in combination with a fluorometer, the receiving end of said fluorometer being adjacent to said flat surface region.

4. The body of claim 1 together with a second separate nonparticulate, nonswellable, impermeable, continuous, flat surface region covalently attached to one other diagnostic reagent bound to at least one biologically derived sample labelled with a fluorochrome, said other diagnostic reagent being covalently attached to said second surface region.

5. The body of claim 4 in which said second region comprises a standard region including a predetermined quantity of said fluorochrome labelled sample type of substance.

6. The body of claim 5 in which said surface region is polyhedral and has a different one of said labelled sample type of substances on a plurality of its face.

7. In a method for the fluorometric detection of an unknown quantity of a biologically derived sample, the steps of:
    (a) covalently attaching a diagnostic reagent to at least one nonparticulate, nonswellable, impermeable continuous, flat surface region of a body,
    (b) contacting the reagent-bonded flat surface of step (a) with a sample substance reactive with said diagnostic reagent in solution and with a fluorochrome labelled substance in solution for a sufficient time to form a fluorochrome labelled reaction product capable of detection,
    (c) separating the reacted surface and solution containing unbound fluorochrome labelled substance after completion of step (b),
    (d) washing the reacted surface of step (c); and
    (e) transporting the body to the detection station of a fluorometer to quantitatively measure the amount of fluorescence emitted from the washed reacted surface of step (d).

8. The method of claim 7 in which in step (c) sample substance contact is performed by gripping the body by a handle attached thereto, contacting the diagnostic reagent-bonded surface with a container of solution of sample substance, and moving said surface relative to said body of solution.

9. The method of claim 7 in which the body is dipped into said container of solution and movement is performed by stirring with the handle portion.

10. The method of claim 7 in which the body is dipped into said container of solution and said movement is performed by agitating said container.

11. The method of claim 7 in which in step (c) said sample substance is reacted with said diagnostic reagent and washed prior to reaction with said labelled substance, said latter substance being reactive with said sample substance.

12. The method of claim 7 in which in step (c) said sample substance is simultaneously reacted with said diagnostic reagent and labelled substance, said latter substance being reactive with said diagnostic reagent.

13. In a method for the fluorometric detection of an unknown quantity of a biologically derived sample, the steps of:
    (a) covalently attaching a diagnostic reagent to at least one nonparticulate, nonswellable, impermeable continuous, flat surface region of a body,
    (b) contacting the reagent-bonded surface of step (a) with a fluorescently labelled sample substance reactive with said diagnostic reagent in solution for a sufficient time to form a fluorescent reaction product capable of fluorometric detection,
    (c) separating the reacted surface and solution containing unbound labelled sample substance after completion of step (b),
    (d) washing the reacted surface of step (c); and
    (e) transporting the body to the detection station of a fluorometer to measure the amount of labelled substance on the washed reacted surface of step (d).

* * * * *